(12) United States Patent
Cannamela et al.

(10) Patent No.: US 12,702,766 B2
(45) Date of Patent: Aug. 11, 2026

(54) DRUG DELIVERY DEVICES WITH REUSABLE COMPONENTS AND DISPOSABLE COMPONENTS

(71) Applicant: JANSSEN PHARMACEUTICA NV, Beerse (BE)

(72) Inventors: Michael Cannamela, Highland, NJ (US); Hong Yan, Livermore, CA (US); Dolores Perez, Eaton, PA (US); Jimmy Vinh Hoang Cassebee, Fremont, CA (US); Emma Louise Hubert, San Jose, CA (US); Steven M. Vesole, San Bruno, CA (US); Shagun Popli, Pleasanton, CA (US); Jingli Wang, San Jose, CA (US)

(73) Assignee: JANSSEN PHARMACEUTICA NV, Beerse (CH)

( * ) Notice: Subject to any disclaimer, the term of this patent is extended or adjusted under 35 U.S.C. 154(b) by 675 days.

(21) Appl. No.: 18/023,649

(22) PCT Filed: Sep. 1, 2021

(86) PCT No.: PCT/EP2021/074092

§ 371 (c)(1),
(2) Date: Feb. 27, 2023

(87) PCT Pub. No.: WO2022/049103

PCT Pub. Date: Mar. 10, 2022

(65) Prior Publication Data

US 2024/0009409 A1 Jan. 11, 2024

Related U.S. Application Data

(60) Provisional application No. 63/073,002, filed on Sep. 1, 2020.

(51) Int. Cl.
*A61M 15/00* (2006.01)
*A61M 11/00* (2006.01)
*A61M 15/08* (2006.01)

(52) U.S. Cl.
CPC ...... *A61M 15/0003* (2014.02); *A61M 11/006* (2014.02); *A61M 15/0028* (2013.01); *A61M 15/08* (2013.01); *A61M 2205/50* (2013.01)

(58) Field of Classification Search
CPC ............ A61M 15/0003; A61M 11/006; A61M 15/0028; A61M 15/08; A61M 2205/50;
(Continued)

(56) References Cited

U.S. PATENT DOCUMENTS 6,708,846 B1 3/2004 Fuchs et al.
7,258,119 B2 8/2007 Mazzoni
(Continued)

FOREIGN PATENT DOCUMENTS

WO 2012123819 A1 9/2012
WO 2015025324 A1 2/2015

OTHER PUBLICATIONS

Invitation to Pay Additional Fees, received for PCT Application No. PCT/EP2021/074092, mailed on Jan. 11, 2022, 24 pages.

*Primary Examiner* — Timothy A Stanis
*Assistant Examiner* — Matthew R Moon
(74) *Attorney, Agent, or Firm* — Craig M. Brown

(57) ABSTRACT

Various exemplary drug delivery devices (500, 700) with reusable components (512, 702) and disposable components (504, 704, 706), drug products utilizing the same, and methods of using drug delivery devices with reusable components and disposable components are provided. In general, a nasal drug delivery device is configured to deliver a drug therefrom and includes one or more disposable components and one or more reusable components. The one or
(Continued)

more disposable components are releasably coupled to the one or more reusable components. After the drug is delivered from the drug delivery device, the one or more disposable components can be detached from the one or more reusable components. Another one or more disposable components can then be releasably coupled to the one or more reusable components and the drug delivery device used to again deliver a drug therefrom.

22 Claims, 7 Drawing Sheets

(58) Field of Classification Search
CPC .............. A61M 15/003; A61M 16/161; A61M 2205/123; A61M 2205/14; A61M 2205/19; A61M 2205/276; A61M 2205/3368; A61M 2205/35; A61M 2205/502; A61M 2205/52; A61M 2205/581; A61M 2205/583; A61M 2205/586; A61M 2205/82; A61M 2209/06; A61M 11/007; A61M 5/30; A61M 5/3007; A61M 5/3015; G16H 20/13; G16H 40/63
See application file for complete search history.

(56) References Cited

U.S. PATENT DOCUMENTS

| | | | | |
|---|---|---|---|---|
| 2005/0256182 | A1 | 11/2005 | Sutter et al. | |
| 2016/0199598 | A1* | 7/2016 | Curtis | A61M 15/0045 128/203.15 |
| 2016/0199599 | A1 | 7/2016 | Isaacs et al. | |
| 2016/0354558 | A1* | 12/2016 | Seguin | A61M 39/22 |
| 2018/0133415 | A1* | 5/2018 | Esteve | B05B 15/40 |
| 2019/0151579 | A1 | 5/2019 | Kohring et al. | |
| 2019/0201290 | A1* | 7/2019 | Denenburg | A61J 1/2031 |
| 2020/0179378 | A1* | 6/2020 | Kollins | A61K 9/14 |
| 2020/0197633 | A1 | 6/2020 | Shahaf et al. | |

* cited by examiner

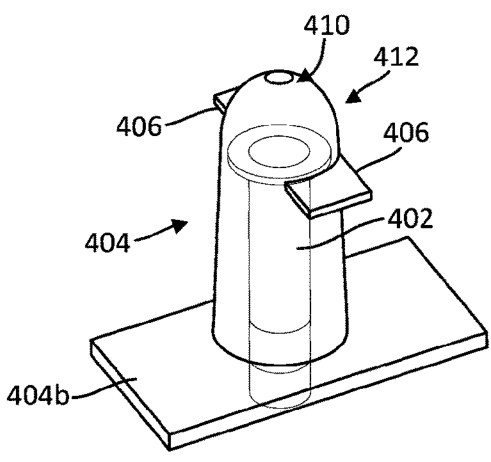
FIG. 5
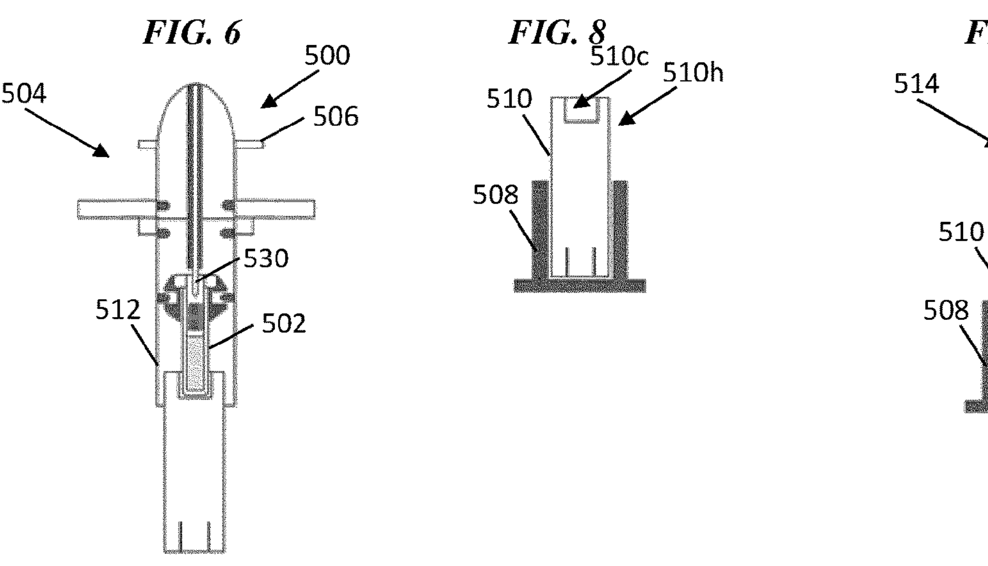
FIG. 6
FIG. 8
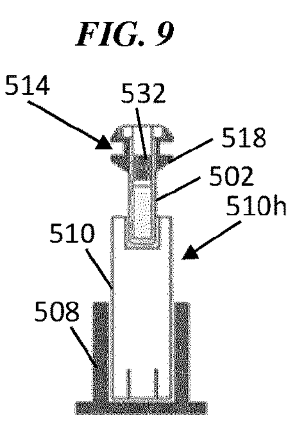
FIG. 9

506
504
518
528
502
Dispose
512
520
516
516
508
510
Reuse

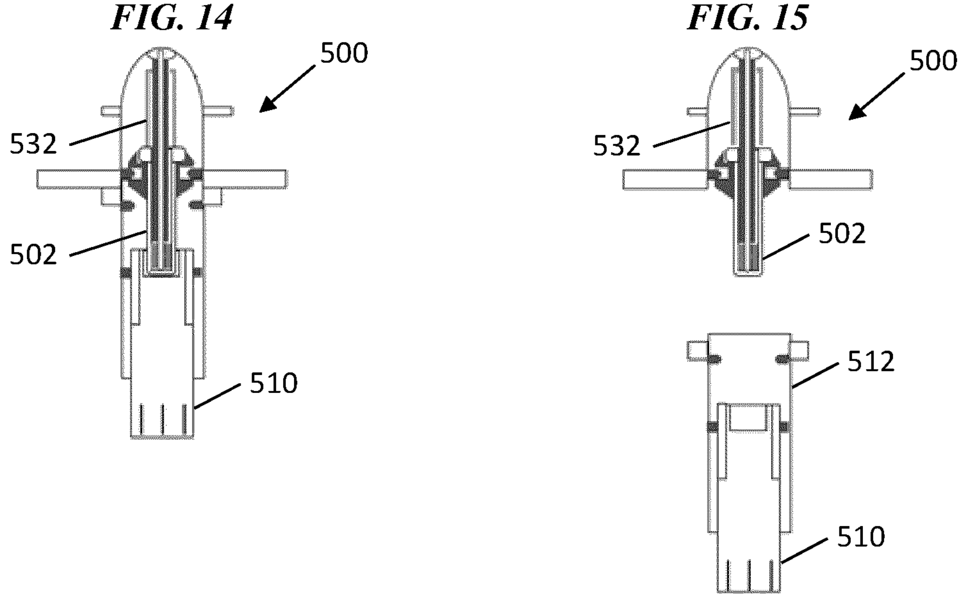
FIG. 14
500
532
502
510
FIG. 15
500
532
502
512
510
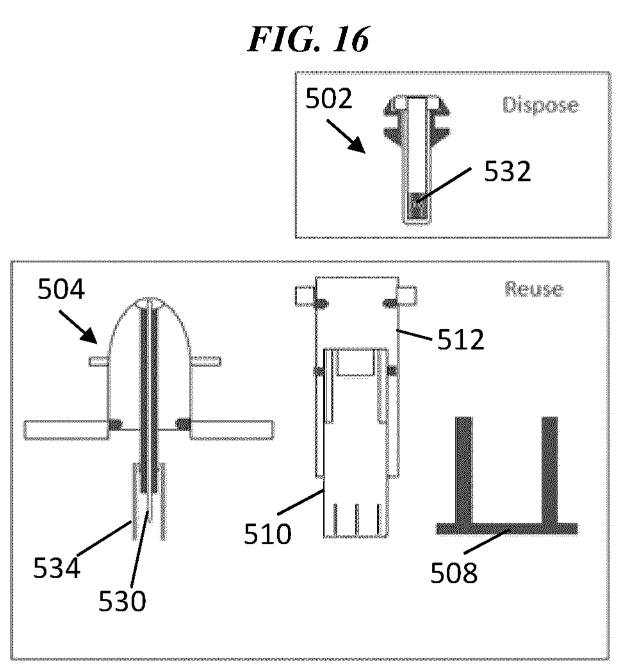
FIG. 16
502
Dispose
532
504
Reuse
512
510
534
530
508

DRUG DELIVERY DEVICES WITH REUSABLE COMPONENTS AND DISPOSABLE COMPONENTS

CROSS REFERENCE TO RELATED APPLICATIONS

This application is the U.S. national stage of PCT Application No. PCT/EP2021/074092, filed Sep. 1, 2021, which claims priority to U.S. Provisional Patent Application No. 63/073,002, filed Sep. 1, 2020, the entire contents of each of which are hereby incorporated by reference in their entirety.

FIELD

The present disclosure relates generally to drug delivery devices with reusable components and disposable components, and drug products utilizing the same.

BACKGROUND

There are many different ways in which a drug can be administered to a user. Depending on the drug, intranasal drug delivery can be one of the most effective ways to achieve desired clinical benefits in a timely manner and in a manner that is convenient and comfortable for a patient.

Intranasal drug administration is a non-invasive route for drug delivery. Since the nasal mucosa offers numerous benefits as a target tissue for drug delivery, a wide variety of drugs may be administered by intranasal systemic action. Moreover, intranasal drug delivery can avoid the risks and discomfort associated with other routes of drug delivery, such as intravenous drug delivery, and can allow for easy self-administration.

Generally, to maximize the efficacy of the drug through intranasal administration, the majority volume of the aerosolized dose of the drug needs to reach the correct region of the nasal cavity. As such, additional measures may need to be taken for effective intranasal drug delivery. For example, the user may need to have a clear nostril, tilt their head back at approximately 45°, close the opposite nostril, and then sniff gently while the dose of drug is administered. In order to coordinate these measures, and given that nasal administration is intimate, self-administration by the user may be desired. Further, due to the nasal cycle (alternating physiological partial congestion of the nasal turbinate to facilitate nasal function) or pathological congestion, one nostril is likely to provide a more effective drug delivery route than the other nostril at any given time. As such, it is desired that an equal dose of the drug be delivered to each nostril of the user to inhibit under-dosing of the drug.

Dual-dose intranasal drug delivery devices are available that are designed for self-administration of two distinct aerosolized sprays, one for each nostril, that together constitute one dose of drug. These devices require a series of operational steps that the user needs to properly carry out to effect optimal drug delivery through self-administration. After the drug is delivered, the device may be disposed of as a used device having no drug remaining in the device or having a residual amount of the drug remaining in the device that cannot be further delivered from the device. Disposing the device after use may have adverse environmental impacts by generating waste that cannot be recycled, that is accidentally not recycled, or that cannot be efficiently recycled from the particular geographic region of the device's use. Some nasal drug delivery devices are designed for one-time use to deliver one dose of drug, such as for prescription drugs where the amount of drug delivered to the patient is important and is typically prescribed at a certain amount per dose. Such one-time use devices may therefore have exacerbated adverse environmental impacts since they are not reused before disposal.

Additionally, one-time use nasal drug delivery devices prevent patients from becoming familiar and comfortable with using the same device for multiple drug deliveries. Even if each sequentially used nasal drug delivery device is the same as one another, at least some patients may not recognize each device's similarity and/or may feel reluctance and/or nervousness at using a device they have never used before.

Accordingly, there remains a need for improved nasal drug delivery devices.

SUMMARY

In general, drug delivery devices with reusable components and disposable components, drug products utilizing the same, and methods of using drug delivery devices with reusable components and disposable components are provided.

In one aspect, a drug delivery system is provided that in one embodiment includes a dispensing head including a tip configured to be positioned in a nose of a patient. The tip has an opening therein. The drug delivery system also includes a drug holder containing a drug therein, and a body including a distal coupling feature configured to releasably couple to a coupling mechanism of the drug holder. The body also includes a proximal coupling feature configured to releasably couple to a coupling mechanism of the dispensing head. After the drug has been delivered out of the opening, the drug holder and the dispensing head are configured to be released from the proximal coupling feature as a unit.

The drug delivery system can have any number of variations. For example, the drug holder can be configured to be at least partially disposed within the dispensing head after the drug has been delivered out of the opening to allow the drug holder and the dispensing head to be released from the proximal coupling feature as the unit after the drug has been delivered out of the opening. For yet another example, the proximal coupling feature can include a thread, and the coupling mechanism of the dispensing head can include a thread configured to mate with the thread of the proximal coupling feature. For another example, the coupling mechanism of the dispensing head can include a clip configured to clip to the proximal coupling feature. For yet another example, one of the proximal coupling feature and the coupling mechanism of the dispensing head can include one or more protrusions, and the other of the proximal coupling feature and the coupling mechanism of the dispensing head can include one or more grooves or depressions configured to seat the one or more protrusions therein. For still another example, the coupling mechanism of the dispensing head can be on a distal base of the dispensing head that can be configured to be manually pressed by a user to cause the drug to be delivered out of the opening. For another example, the drug delivery system can include a depth guide attached to the dispensing head configured to facilitate guiding the tip into the nose at a depth. For still another example, the drug can be one of ketamine, esketamine, naloxone, and sumatriptan.

For yet another example, the drug delivery system can include a second dispensing head including a second tip configured to be positioned in the nose of the patient, the second tip can have a second opening therein, the drug delivery system can include a second drug holder containing a second drug therein, a second coupling mechanism of the second drug holder can be configured to releasably couple to the distal coupling feature after the drug holder and the dispensing head have been released from the proximal coupling feature, a second coupling mechanism of the second dispensing head can be configured to releasably couple to the proximal coupling feature after the drug holder and the dispensing head have been released from the proximal coupling feature, and, after the second drug has been delivered out of the second opening, the second drug holder and the second dispensing head can be configured to be released from the proximal coupling feature as a unit. The drug can be one of ketamine, esketamine, naloxone, and sumatriptan, and the second drug can be one of ketamine, esketamine, naloxone, and sumatriptan. The drug and the second drug can be the same or can be different.

In another aspect, a drug product is provided that in one embodiment includes a drug product disposed in a drug delivery system. The drug delivery system includes a dispensing head including a tip configured to be positioned in a nose of a patient. The tip has an opening therein. The drug delivery system also includes a drug holder containing the drug product therein, and a body including a distal coupling feature configured to releasably couple to a coupling mechanism of the drug holder. The body also includes a proximal coupling feature configured to releasably couple to a coupling mechanism of the dispensing head. After the drug product has been delivered out of the opening, the drug holder and the dispensing head are configured to be released from the proximal coupling feature as a unit. The drug product is one of ketamine, esketamine, naloxone, and sumatriptan. The drug delivery system can have any number of variations.

In another embodiment, a drug delivery system is provided that includes a proximal member including a tip configured to be positioned in a nose of a patient. The tip has an opening therein, and the proximal member includes a coupling mechanism. The drug delivery system also includes a first distal member containing a first drug therein. The first distal member includes a first plunger configured to be actuated to cause the first drug to exit the first distal member, and the first distal member includes a first coupling feature configured to releasably couple the first distal member to the proximal member. The drug delivery system also includes a second distal member containing a second drug therein. The second distal member includes a second plunger configured to be actuated to cause the second drug to exit the second distal member, and the second distal member includes a second coupling feature configured to releasably couple the second distal member to the proximal member.

The drug delivery system can have any number of variations. For example, the proximal member can be configured to simultaneously have the first and second distal members releasably coupled thereto. The proximal member can include a first cavity therein that is configured to releasably seat the first distal member therein, and the proximal member can include a second cavity therein that is configured to releasably seat the second distal member therein.

For another example, the proximal member can be configured to have only one of the first and second distal members releasably coupled thereto at a time. The proximal member can include a cavity therein that is configured to sequentially seat the first distal member and the second distal member therein.

For yet another example, the first coupling feature can include a thread, and the proximal member can include a thread configured to mate with the thread of the first coupling feature. The second coupling feature can includes a thread, and the proximal member can include an additional thread configured to mate with the thread of the second coupling feature such that the proximal member is configured to be releasably coupled to the first and second distal members simultaneously, or the thread of the proximal member can be configured to be threaded with only one of the thread of the first coupling feature and the thread of the second coupling feature at a time.

For still another example, the first drug can be one of ketamine, esketamine, naloxone, and sumatriptan, and the second drug can be one of ketamine, esketamine, naloxone, and sumatriptan. The first drug and the second drug can be the same or can be different.

In another aspect, a drug product is provided that in one embodiment includes a drug product disposed in a drug delivery system. The drug delivery system includes a proximal member including a tip configured to be positioned in a nose of a patient. The tip has an opening therein, and the proximal member includes a coupling mechanism. The drug delivery system also includes a first distal member containing a first drug of the drug product therein. The first distal member includes a first plunger configured to be actuated to cause the first drug to exit the first distal member, and the first distal member includes a first coupling feature configured to releasably couple the first distal member to the proximal member. The drug delivery system also includes a second distal member containing a second drug of the drug product therein. The second distal member includes a second plunger configured to be actuated to cause the second drug to exit the second distal member, and the second distal member includes a second coupling feature configured to releasably couple the second distal member to the proximal member. The drug product is one of ketamine, esketamine, naloxone, and sumatriptan. The drug delivery system can have any number of variations.

In another aspect, a drug delivery method is provided in that in one embodiment includes coupling a first dispensing head to a first coupling feature of a body, and coupling a first drug holder to a second coupling feature of the body. The first drug holder contains a first drug therein. The drug delivery method also includes, after coupling the first dispensing head and the first drug holder to the body, causing the first drug to exit the first drug holder and spray out an opening of a tip of the first dispensing head that is positioned in a nose of a patient. The drug delivery method also includes removing the first dispensing head and the first drug holder as a unit from the body and subsequently coupling a second dispensing head to the first coupling feature of the body and coupling a second drug holder to the second coupling feature of the body. The second drug holder contains a second drug therein. The drug delivery method also includes, after coupling the second dispensing head and the second drug holder to the body, causing the second drug to exit the second drug holder and spray out a second opening of a second tip of the second dispensing head that is positioned in the nose of the patient.

The drug delivery method can vary in any number of ways. For example, the drug holder can be at least partially disposed within the dispensing head after the first drug has exited the drug holder to allow the drug holder and the first dispensing head to be removed as the unit. For yet another example, the first coupling feature can include a thread, and coupling the first dispensing head to the body can include mating the first dispensing head to the thread of the first coupling feature. For another example, coupling the first dispensing head to the body can include clipping the first dispensing head to the first coupling feature. For yet another example, the first coupling feature can include one or more protrusions, and coupling the first dispensing head to the body can include seating the one or more protrusions in one or more grooves or depressions of the dispensing head. For still another example, the first coupling feature can include one or more grooves or depressions, and coupling the first dispensing head to the body can include seating one or more protrusions of the dispensing head in the one or more grooves or depressions. For another example, causing the first drug to exit the first drug holder can include pushing the first dispensing head relative to the body, and causing the second drug to exit the second drug holder can include pushing the second dispensing head relative to the body.

For yet another example, the drug can be one of ketamine, esketamine, naloxone, and sumatriptan, and the second drug can be one of ketamine, esketamine, naloxone, and sumatriptan. The first drug and the second drug can be the same or can be different.

In another embodiment, a drug delivery method is provided that includes coupling a proximal member to a first distal member containing a first drug therein, coupling the proximal member to a second distal member containing a second drug therein, and, after coupling the first and second distal members to the proximal member, causing the first drug to exit the first distal member and spray out an opening of a tip of the proximal member that is positioned in a nose of a patient, and subsequently causing the second drug to exit the second distal member and spray out the opening of the tip of the proximal member that is positioned in the nose of the patient. The drug delivery method also includes, after causing the first drug to exit the first distal member, removing the first distal member from the proximal member and subsequently coupling a third distal member to the proximal member, the third distal member containing a third drug therein. The drug delivery method also includes, after causing the second drug to exit the second distal member, removing the second distal member from the proximal member and subsequently coupling a fourth distal member to the proximal member, the fourth distal member containing a fourth drug therein.

The method can have any number of variations. For example, coupling the proximal member to the first distal member can include threading the proximal member and the first distal member together, and coupling the proximal member to the second distal member can include threading the proximal member and the second distal member together. For another example, causing the first drug to exit the first distal member can include actuating a first plunger of the first distal member, and causing the second drug to exit the second distal member can include actuating a second plunger of the second distal member.

For yet another example, the first drug can be one of ketamine, esketamine, naloxone, and sumatriptan, and the second drug can be one of ketamine, esketamine, naloxone, and sumatriptan. The first drug and the second drug can be the same. The first, second, third, and fourth drugs can be the same. The first drug and the second drug can be different. The first, second, third, and fourth drugs can be different.

BRIEF DESCRIPTION OF DRAWINGS

The present invention is described by way of reference to the accompanying figures which are as follows:

FIG. 5 is a perspective view of disposable components of the drug delivery device of FIG. 4;

FIG. 6 is a side cross-sectional view of another embodiment of the drug delivery device of FIG. 2;

FIG. 8 is a side cross-sectional view of an actuator of the drug delivery device of FIG. 6 coupled to one embodiment of a loading accessory;

FIG. 9 is a side cross-sectional view of a drug holder of the drug delivery device of FIG. 6 coupled to the actuator of FIG. 8;

FIG. 10 is a side cross-sectional view of the drug delivery device of FIG. 6 coupled to the loading accessory of FIG. 9;

FIG. 11 is a side cross-sectional view of the drug delivery device of FIG. 6 delivering a first drug spray;

FIG. 12 is a side cross-sectional view of the drug delivery device of FIG. 11 after delivering the first drug spray;

FIG. 13 is a side cross-sectional view of the drug delivery device of FIG. 12 delivering a second drug spray;

FIG. 14 is a side cross-sectional view of the drug delivery device of FIG. 6 including a shield;

FIG. 15 is an exploded view of the drug delivery device of FIG. 14;

FIG. 16 is an exploded side cross-sectional view of the drug delivery device of FIG. 14 including disposable components and reusable components;

DETAILED DESCRIPTION

Figure 1:
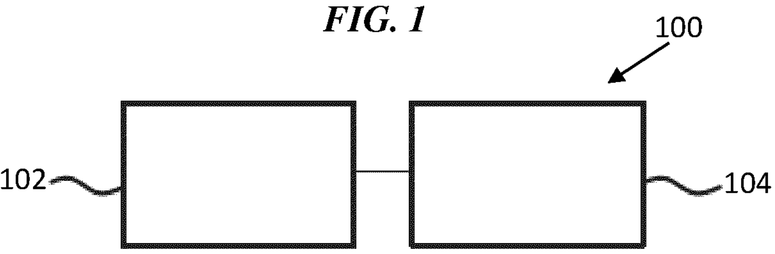
FIG. 1 is a block diagram of one embodiment of a drug delivery device.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary drug delivery devices with reusable components and disposable components, drug products utilizing the same, and methods of using drug delivery devices with reusable components and disposable components are provided. In general, a nasal drug delivery device is configured to deliver a drug therefrom and includes one or more disposable components and one or more reusable components. The one or more disposable components are releasably coupled to the one or more reusable components. After the drug is delivered from the drug delivery device, the one or more disposable components can be detached from the one or more reusable components. Another one or more disposable components can then be releasably coupled to the one or more reusable components and the drug delivery device used to again deliver a drug therefrom. This replacement process can occur any number of additional times, e.g., zero, one, two, three, four, five, six, etc.

Replacing one or more components of the drug delivery device, e.g., the one or more disposable components, after drug delivery allows a remainder of the drug delivery device, e.g., the one or more reusable components, to be re-used, thereby generating less waste than drug delivery devices that are disposed of after use. Replacing the one or more components of the drug delivery device of the drug delivery device after drug delivery allows for a standard portion of the drug delivery device to be purchased that can be used for a plurality of dose deliveries instead of requiring multiple drug delivery devices to be purchased to deliver that same number of doses, thereby saving the purchaser money since fewer drug delivery devices need to be purchased. The standard portion of the drug delivery device is defined by the one or more reusable components. Replacing the one or more disposable components of the drug delivery device allows for the standard portion of the drug delivery device to be repeatedly used by the same user for a plurality of dose deliveries, which may allow for the user to develop familiarity and confidence in the device over time and/or may reduce user reluctance and/or nervousness in using the drug delivery device since (after the first use) they are not using a device they have never used before.

In an exemplary embodiment, the one or more disposable components of the drug delivery device include a dispensing head of the drug delivery device that includes a tip configured to be inserted into a nostril of a patient. The tip includes an opening through which the drug is configured to spray from the drug delivery device and into the patient's nose. Disposing and replacing the dispensing head may reduce user reluctance, nervousness, and/or hygiene concerns in using the drug delivery device since a new tip can be inserted into their nose for each drug spray or after a total dose achieved by delivering a plurality of sprays has been delivered from the drug delivery device.

In an exemplary embodiment, the one or more reusable components of the drug delivery device include an actuator of the drug delivery device that is configured to be actuated to cause the start of drug delivery. Reusing the actuator may become familiar with use of the drug delivery device over time by having multiple tactile experiences therewith, e.g., with each actuation of the actuator. The drug delivery device may therefore be less likely to be accidentally actuated and cause drug waste and/or to be misused with drug delivery not occurring properly or at all.

In an exemplary embodiment, the one or more reusable components of the drug delivery device are fixedly attached to one another. The one or more reusable components being fixedly attached to one another may help ensure that this reusable portion of the drug delivery device is not tampered with and/or remains consistently assembled, and hence consistently used, when different sets of one or more reusable components are coupled thereto.

In an exemplary embodiment, the one or more reusable components of the drug delivery device is usable to deliver subsequent doses of the same drug to a user. The user may therefore be able to use the same reusable drug delivery device component(s) repeatedly in fulfilling a drug prescription. In other embodiments, the drug delivered by the drug delivery device is not the same in each use of the one or more reusable components of the drug delivery device such that the one or more reusable components of the drug delivery device are usable to deliver doses of different drugs to a user of the drug delivery device. The user may therefore be able to use the same reusable drug delivery device component(s) repeatedly in fulfilling two or more drug prescriptions.

The drug to be delivered using a drug delivery device as described herein can be any of a variety of drugs. Examples of drugs that can be delivered using a drug delivery device as described herein include antibodies (such as monoclonal antibodies), hormones, antitoxins, substances for the control of pain, substances for the control of thrombosis, substances for the control of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying anti-rheumatic drugs, erythropoietin, and vaccines. Examples of drugs that can be delivered using a drug delivery device as described herein include ketamine (e.g., Ketalar®), esketamine (e.g., Spravato®, Ketanest®, and Ketanest-S®), naloxone (e.g., Narcan®), and sumatriptan (e.g., Imitrex®).

A drug delivery device including one or more disposable components and one or more reusable components can have a variety of configurations. In general, the drug delivery device is configured to deliver a drug to a patient, where the drug is provided in a defined dosage form within the drug delivery device.

FIG. 1 illustrates one embodiment of a drug delivery device 100 including one or more disposable components 102 and one or more reusable component 104. As will be appreciated by a person skilled in the art, the drug delivery device 100 can include different features in different embodiments depending upon various requirements, such as the type of drug, typical dosage(s) of the drug, safety requirements in various jurisdictions, whether the drug delivery device is powered, etc.

Figure 2:
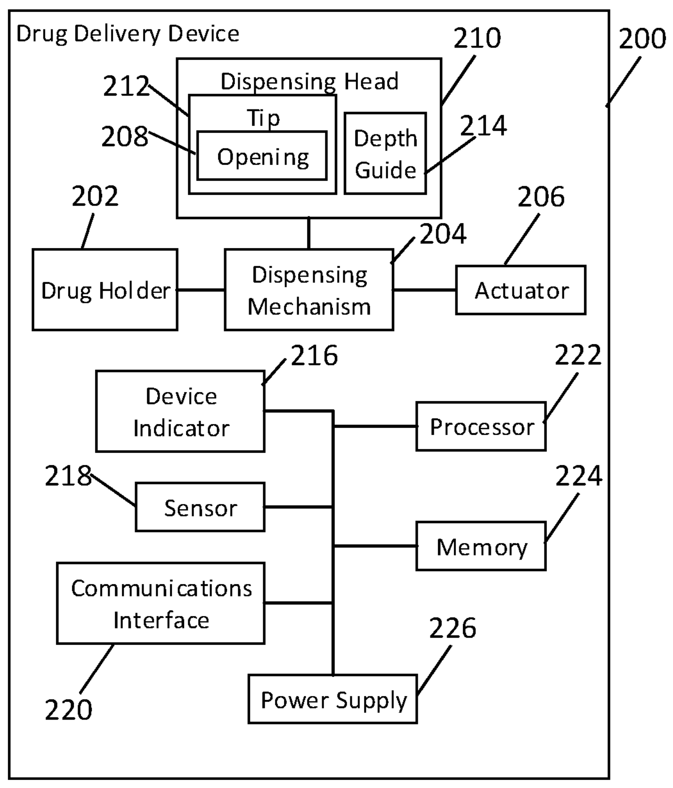
FIG. 2 is a block diagram of one embodiment of the drug delivery device of FIG. 1.

FIG. 2 illustrates an exemplary embodiment of the drug delivery device 100 of FIG. 1. FIG. 2 illustrates a drug delivery device 200 that includes a coupling mechanism configured to releasably couple one or more reusable components of the drug delivery device 200 with one or more disposable components of the drug delivery device 200. The coupling mechanism can have a variety of configurations, as discussed further below. The one or more reusable components and the one or more disposable components can vary, as also discussed further below.

The drug delivery device 200 includes a drug holder 202 configured to contain a drug therein for delivery from the device 200 to a patient. The drug holder 202 can have a variety of configurations, such as a cartridge, a vial, a blow-fill-seal (BFS) capsule, etc. In an exemplary embodiment, the drug holder 202 is a vial. An exemplary vial is formed of one or more materials, e.g., glass, polymer(s), etc. In some embodiments, a vial can be formed of glass. In other embodiments, a vial can be formed of one or more polymers. In yet other embodiments, different portions of a vial can be formed of different materials.

Figure 3:
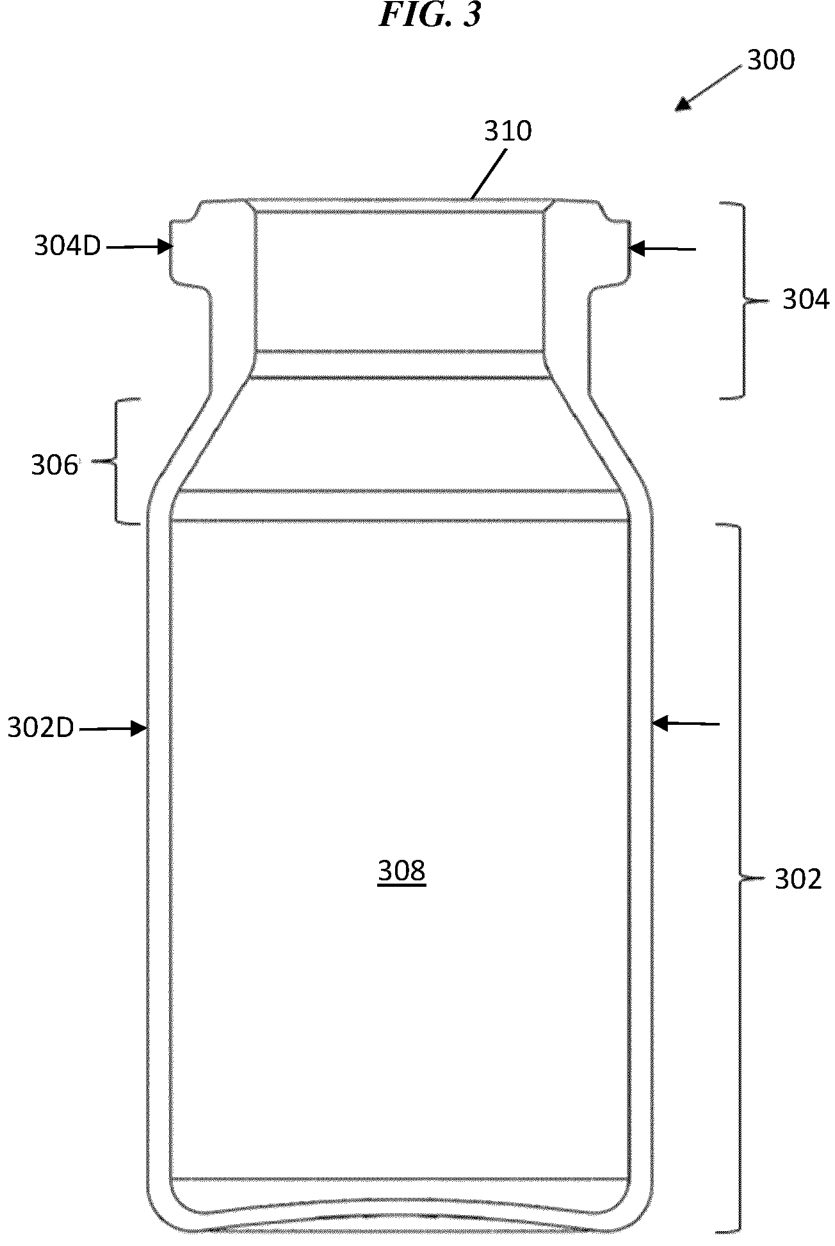
FIG. 3 is a side cross-sectional view of one embodiment of a vial.

FIG. 3 illustrates an exemplary embodiment of the drug holder 202 in the form of a vial 300 configured to contain a drug therein. The vial 300 includes a base or distal portion 302 and a head or proximal portion 304. As shown, the vial 300 also includes an inwardly tapering neck portion 306 that extends between the base portion 302 and the head portion 304. The inwardly tapering neck portion 306 allows the head portion 304 to have a maximum outer diameter 304D that is less than a maximum outer diameter 302D of the base portion 302. In other embodiments, the taper between the base and head portions 302, 304 can be omitted, and the base and head portions 302, 304 can have a same maximum outer diameter 302D, 304D as one another. The head portion 304 having a smaller maximum outer diameter 304D than the base portion's maximum outer diameter 302D may ease coupling of the vial 300 to a drug delivery device in embodiments in which the vial 300 is one of the drug delivery device's one or more disposable components. For example, a user can hold the base portion 302 and insert the vial 300 proximally into the drug delivery device by providing a larger area of the vial 300 for the user to hold (e.g., the base portion 302) and a smaller area of the vial 300 to lead the insertion of the vial 300 into the drug delivery device (e.g., the head portion 304).

The base portion 302 defines a hollow interior 308 within the base portion 302 that is configured to contain the drug therein. In an exemplary embodiment, an amount of the drug in the vial 300 is such that the drug can be contained entirely within the hollow interior 308 of the base portion 302, but the amount of the drug can be such that drug entirely fills the hollow interior 308 of the base portion 302 and also fills at least some part of the neck portion 306 and optionally also at least some part of the head portion 304. While the base portion 302 can have a variety of configurations, in this illustrated embodiment, the base portion 302 has a substantially cylindrical shape. In other embodiments, the base portion 302 can have any other suitable shapes, e.g., a substantially rectangular shape, etc. A person skilled in the art will appreciate that a shape may not be a precise shape (e.g., a precise cylinder or a precise rectangle) but nevertheless be considered to be substantially that shape due to any number of factors, such as manufacturing tolerances and sensitivity of measurement equipment.

The vial 300 includes a seal member 310 at a proximal end thereof in the head portion 304. The seal member 310 is configured to provide a fluid tight seal such that the drug is contained in the vial 300 until the seal provided by the seal member 310 is broken. The seal provided by the seal member 310 can be broken in a variety of ways, such as by being pierced by a needle, pin, piston, etc. of the drug delivery device to which the vial 300 is releasably coupled. The seal member 310 can have a variety of configurations, as will be appreciated by a person skilled in the art, such as by being a pierceable polymer septum or a foil layer. The seal member 310 can be protected from accidental puncturing or piercing before intended use with a removable protective member or stopper, such as a tamper evident (TE) seal, etc. In some embodiments, the seal member 310 can be omitted and instead a removable protective member or stopper can be provided that is removed just prior to use of the vial 300.

An exemplary vial can include a variety of features to facilitate sealing and storing a drug therein, as described herein and illustrated in the drawings. However, a person skilled in the art will appreciate that the vials can include only some of these features and/or can include a variety of other features known in the art. The vials described herein are merely intended to represent certain exemplary embodiments.

Referring again to FIG. 2, the drug delivery device 200 also includes a dispensing mechanism 204 that is configured to be operatively coupled to the drug holder 202 and that is configured to release a drug from the drug delivery device 200, e.g., from the drug holder 202, so that the drug can be administered to a patient. The dispensing mechanism 204 can have a variety of configurations. For example, the dispensing mechanism 204 can include a piercing element, e.g., a piston, pin, and/or a needle, configured to pierce through or puncture a seal member of the drug holder 202 to gain access to the drug contained in the drug holder 202.

The drug delivery device 200 also includes an actuator 206 configured to be actuated by a user to cause the dispensing mechanism 204 to begin delivering a dose of the drug through an opening or nozzle 208 in the drug delivery device 200. In an exemplary embodiment, the drug delivery device 200 is configured to be self-administered such that the user who actuates the actuator 206 is the patient receiving the drug from the drug delivery device 200.

The opening 208 through which the drug exits the drug delivery device 200 is formed in a dispensing head 210 of the drug delivery device 200 in a tip 212 of the dispensing head 210. The tip 212 is configured to be inserted into a nostril of a patient. In an exemplary embodiment, the tip 212 is configured to be inserted into a first nostril of the patient during a first stage of operation of the drug delivery device 200 and into a second nostril of the patient during a second stage of operation of the drug delivery device 200. The first and second stages of operation involve two separate actuations of the actuator 206, a first actuation corresponding to a first dose of the drug being delivered and a second actuation corresponding to a second dose of the drug being delivered. The dispensing head 210 includes a depth guide 214 configured to contact skin of the patient, e.g., between the patient's first and second nostrils, such that a longitudinal axis of the dispensing head 210 is substantially aligned with a longitudinal axis of the nostril in which the tip 212 is inserted. A person skilled in the art will appreciate that the longitudinal axes may not be precisely aligned but nevertheless be considered to be substantially aligned due to any number of factors, such as manufacturing tolerances and sensitivity of measurement equipment.

In an exemplary embodiment, the dispensing head 210 has a tapered shape in which the dispensing head 210 has a smaller diameter at its distal end than at its proximal end where the opening 208 is located. The opening 208 having a relatively small diameter facilitates spray of the drug out of the opening 208, as will be appreciated by a person skilled in the art. A spray chamber through which the drug is configured to pass before exiting the opening 208 is located within a proximal portion of the tapered dispensing head 210, distal to the opening 208. When the drug passes through the spray chamber at speed, the spray chamber facilitates production of a fine mist that exits through the opening 208 with a consistent spray pattern.

In some embodiments, the dispensing head 210 can include two tips 212 each having an opening 208 therein such that the drug delivery device 200 is configured to simultaneously deliver doses of drug into two nostrils in response to a single actuation of the actuator 206.

The drug delivery device 200 also includes a device indicator 216 configured to present information to a user about a status of the drug delivery device 200 and/or the drug contained in the drug holder 202. The device indicator 216 can be a visual indicator, such as a display screen, one or more lights, one or more colored and/or numbered markings, etc. Alternatively or in addition, the device indicator 216 can be an audio indicator configured to provide sound.

The drug delivery device 200 also includes a sensor 218 configured to sense information relating to the drug delivery device 200 and/or the drug contained in the drug holder 202. Examples of information that the sensor 218 can sense include environmental conditions (e.g., temperature, humidity, geographic location, time, etc.) and drug holder status (e.g., whether or not the drug delivery device's one or more reusable components are releasably coupled to the drug delivery device's one or more disposable components). The drug delivery device 200 can also include a communications interface 220 configured to communicate externally data which has been gathered by the sensor 218 about the drug delivery device 200 and/or the drug contained in the drug holder 202, which may facilitate analysis regarding the patient's treatment, patient compliance, use of the drug delivery device 200, etc.

In embodiments in which the drug delivery device 200 includes one or more electrical components, e.g., the device indicator 216 (which in some embodiments can be powered while in other embodiments not be powered), the sensor 218, the communications interface 220, a processor 222, a memory 224, etc., the drug delivery device 200 includes a power supply 226 configured to deliver electrical power to the one or more electrical components of the drug delivery device 200. The power supply 226 can be a source of power which is integral to drug delivery device 200 and/or can be a mechanism configured to connect the drug delivery device 200 to an external source of power. The processor 222 is configured to receive gathered data from the sensor 218 and to cause the data to be stored in the memory 224, to be indicated on the device indicator 210, and/or and to be communicated externally via the communications interface 220. The memory 224 is configured to store instructions that are configured to be executed by the processor 222 for the processor 222 to process information regarding the various electrical components with which the processor 222 is in communication.

As mentioned above, the drug delivery device 200 can include different features in different embodiments depending upon various requirements. For example, the drug delivery device 200 can omit any one or more of the depth guide 214, the device indicator 216, the sensor 218, the communications interface 220, the processor 222, the memory 224, and the power supply 226.

In some embodiments, the one or more disposable components of the drug delivery device 200 include the dispensing head 210, and the one or more reusable components of the drug delivery device 200 include a remainder of the drug delivery device 200. In other embodiments, the one or more disposable components of the drug delivery device 200 include the dispensing head 210 including the tip 212 and opening 208 thereof, and the one or more reusable components of the drug delivery device 200 include a remainder of the drug delivery device 200. In such embodiments, the dispensing head 210 does not include the depth guide 214, rather the depth guide 214 is attached to another portion of the drug delivery device 200, e.g., a body or housing thereof. In yet other embodiments, the one or more disposable components of the drug delivery device 200 include the drug holder 202 and the dispensing head 210, and the one or more reusable components of the drug delivery device 200 include a remainder of the drug delivery device 200. In such embodiments, the drug holder 202 and the dispensing head 210 can be configured to be separately coupled to the one or more reusable components. In still other embodiments, the one or more disposable components of the drug delivery device 200 include the device indicator 216 and the dispensing head 210, and the one or more reusable components of the drug delivery device 200 include a remainder of the drug delivery device 200. In such embodiments, the dispensing head 210 can includes the device indicator 216, e.g., the device locator 216 can be visible on the dispensing head 210. In still other embodiments, the one or more disposable components of the drug delivery device 200 include the device indicator 216, the drug holder 202, and the dispensing head 210, and the one or more reusable components of the drug delivery device 200 include a remainder of the drug delivery device 200. In such embodiments, the dispensing head 210 can include the device indicator 216, and/or in such embodiments, the drug holder 202 and the dispensing head 210 can be configured to be separately coupled to the one or more reusable components.

In embodiments including one or more electronic components, e.g., one or more of the device indicator 216 (in embodiments in which the device indicator 216 is a powered element), the sensor 218, the communications interface 220, the processor 222, the memory 224, and the power supply 226, the one or more reusable components of the drug delivery device 200 can include all of the electronic components. Electronic components may be more expensive than non-electronic components of the drug delivery device 200, so reusing all of the drug delivery device's one or more electronic components may be cost efficient since the one or more electronic components can be re-used. Reusing the drug delivery device's sensor 218 may allow for consistent data gathering since the same sensor 218 will be gathering data over multiple drug deliveries to the patient in which different disposable components are used with the drug delivery device's one or more reusable components, which may facilitate analysis of the patient's treatment, compliance, proper use of the drug delivery device 200, and/or other factors using the gathered data.

The drug delivery device 200 can be provided as part of a kit including the one or more reusable components and one or more sets of the one or more disposable components, e.g., two, three, four, five, six, seven, eight, nine, ten, etc., each configured to be successively coupled to the one or more reusable components. Each of the one or more disposable components can be provided without yet being coupled to the one or more reusable components of the drug delivery device 200, or one of the sets of one or more disposable components can be provided releasably coupled to the one or more reusable components of the drug delivery device 200 with a remainder of the sets of one or more disposable components being provided without yet being coupled to the drug delivery device 200. In embodiments in which the kit includes a plurality of sets of the one or more disposable components, each of the sets can include an order indicator thereon that indicates an order in which the set should be releasably coupled to the one or more reusable components of the drug delivery device 200. For example, the order indicator can include a number printed on each one or more disposable components of the set, etched into each one or more disposable components of the set, printed on a label adhered to each one or more disposable components of, printed on a box or other package containing each one or more disposable components of the set therein, or otherwise made visible to a user of the set. For another example, the order indicator can include a color on each one or more disposable components of, on a label on each one or more disposable components of, on a box or other package containing each one or more disposable components of the set therein, or otherwise made visible to a user of the set. For yet another example, the order indicator can include a number and a color.

Figure 4:
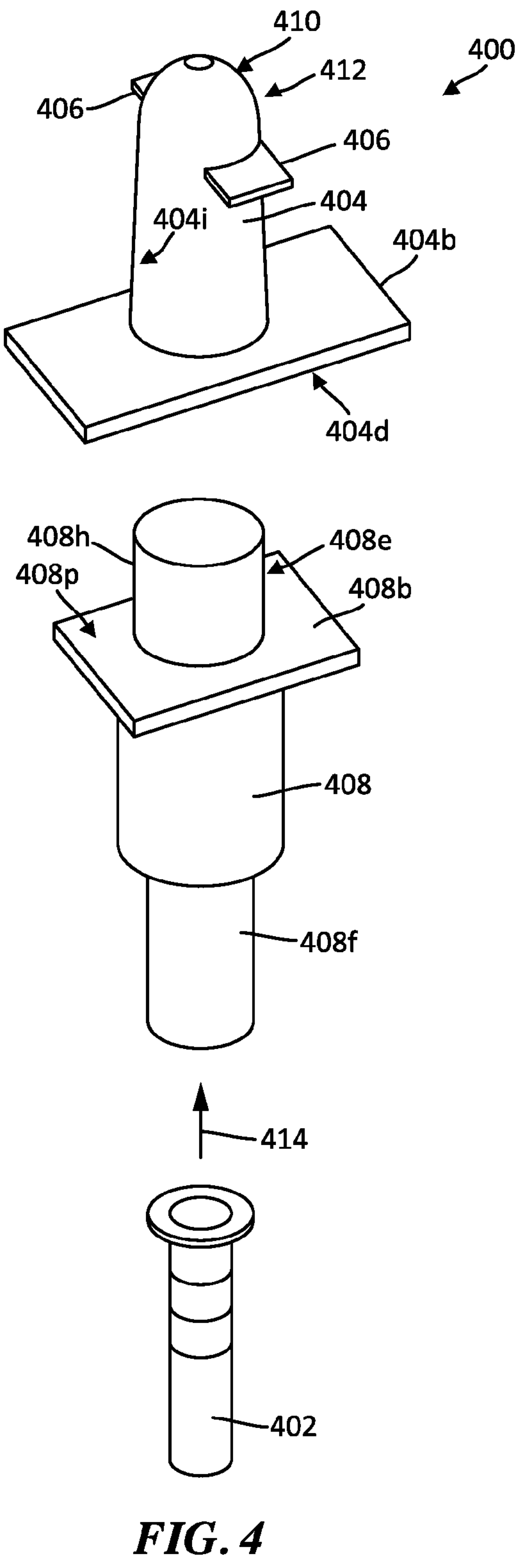
FIG. 4 is an exploded view of one embodiment of the drug delivery device of FIG. 2.

FIG. 4 illustrates an exemplary embodiment of the drug delivery device 200 of FIG. 2 that includes one or more reusable components and one or more disposable components. In this illustrated embodiment of a drug delivery device 400, the one or more disposable components of the drug delivery device 400 include a drug holder 402, a dispensing head 404, and a depth guide 406, and the one or more reusable components 408 of the drug delivery device 400 include a remainder of the drug delivery device 400. The drug holder 402 in this illustrated embodiment is a vial and is generally configured and used similar to the vial 300 of FIG. 3. The dispensing head 404 and the depth guide 406 are integrated together as one element in this illustrated embodiment. In this illustrated embodiment, the one or more reusable components 408 of the drug delivery device 400 are fixedly attached to one another.

The drug delivery device 400 in the illustrated embodiment of FIG. 4 is not powered, e.g., does not include any electrical components such as a processor, a sensor, a memory, a communications interface, etc.

FIG. 4 illustrates the drug holder 402, the dispensing head 404, and the depth guide 406 not coupled to the one or more reusable components 408 of the drug delivery device 400. FIG. 5 illustrates the drug holder 402, the dispensing head 404, and the depth guide 406 decoupled from the one or more reusable components 408 of the drug delivery device 400 after use, e.g., after drug has been delivered from the drug holder 402 through an opening 410 in a tip 412 of the dispensing head 404. The drug holder 402 is disposed at least partially in the dispensing head 404 in FIG. 5, which may facilitate user removal of the one or more disposable components from the one or more reusable components since the one or more disposable components, e.g., the drug holder 402, the dispensing head, and the depth guide 406, can be simultaneously removed from the one or more reusable components of the drug delivery device 400.

The dispensing head 404 includes a coupling mechanism configured to be coupled to a coupling feature of the one or more reusable components 408 of the drug delivery device 400.

As mentioned above and as shown in FIG. 5, the drug holder 402 can be at least partially within the dispensing head 404 after drug delivery, so decoupling the dispensing head 404 (and the depth guide 406 monolithic therewith) from the one or more reusable components 408 in such embodiments can also decouple the drug holder 402 from the one or more reusable components 408. The coupling mechanism and the coupling feature can have a variety of configurations.

For example, the coupling mechanism can include a thread on an internal surface 404*i* of the dispensing head 404, and the coupling feature can include a thread on an external surface 408*e* of the one or more reusable components 408, e.g., on a proximal head 408*h* of the one or more reusable components 408. To couple the dispensing head 404 (and the depth guide 406) to the one or more reusable components 408, the thread on the dispensing head 404 can be releasably mate with the thread on the one or more reusable components 408. The thread on one of the dispensing head 404 and the one or more reusable components can be male, and the thread on the other of the dispensing head 404 and the one or more reusable components can be female.

To decouple the dispensing head 404 (and the depth guide 406) from the one or more reusable components 408, the thread on the dispensing head 404 can be unthreaded from the thread on the one or more reusable components 408.

For another example, the coupling mechanism can include at least one clip on the dispensing head 404, e.g., on a base 404*b* of the dispensing head 404, and the coupling feature can include a surface of the one or more reusable components 408 configured to be clipped by the at least one clip, e.g., a surface of a base 408*b* of the one or more reusable components 408.

To couple the dispensing head 404 (and the depth guide 406) to the one or more reusable components 408, the at least one clip can be releasably clipped to the one or more reusable components 408. To decouple the dispensing head 404 (and the depth guide 406) from the one or more reusable components 408, the at least one clip can be unclipped from the one or more reusable components 408. Alternatively, the coupling feature can include the at least one clip, and the coupling mechanism can include a surface to which the at least one clip of the one or more reusable components 408 is configured to clip to and unclip from.

For yet another example, one of the coupling mechanism and the coupling feature can include one or more protrusions extending therefrom configured to be releasably seated in one or more corresponding grooves or depressions formed in the other of the coupling mechanism and the coupling feature. In such embodiments, the coupling mechanism can be on a distal surface 404*d* of the base 404*b* of the dispensing head, and the coupling feature can be on a proximal surface 408*p* of the base 408*b* of the one or more reusable components 408.

For still another example, the coupling mechanism and the coupling feature can be configured to couple together using a quarter turn cam connection such as a quarter turn cam latch or other quarter turn cam lock.

For yet another example, the coupling mechanism and the coupling feature can be configured to couple together using a bayonet mechanism. One of the coupling mechanism and the coupling feature can include one or more pins or other protrusions that extend radially outward therefrom, and the other of the coupling mechanism and the coupling feature can include one or more corresponding L-shaped slots. The slots can have another shape. Each of the one or more slots can be configured to slidably receive one of the pins therein to releasably couple together the coupling mechanism and the coupling feature. The one or more pins can be removed from their respective slots by being slid out of the slot to decouple the coupling mechanism and the coupling feature.

The drug holder 402 is configured to couple to the one or more reusable components 408 by being advanced proximally into a distal end of the one or more reusable components 408, e.g., into a distal foot 408*f* of the one or more reusable components 408, as shown by an arrow 414 in FIG.

4. An interior cavity extends through the one or more reusable components 408, including through the distal foot 408*f* and the proximal head 408*h* thereof. The drug holder 402 is thus configured to be advanced proximally past the base 408*b* of the one or more reusable components 408 and enter the dispensing head 404. The drug delivery device 400 does not need to be primed after the drug holder 402 has been releasably coupled thereto and prior to actuation of the drug delivery device 400 to cause drug delivery, which may ease use of the drug delivery device 400 by a user.

After the drug has been delivered by the drug delivery device 400, the one or more disposable components can be released from the one or more reusable components 408. The release of the one or more disposable components can vary depending on the coupling mechanism of the one or more disposable components and the coupling feature of the one or more reusable components 408, as discussed above.

In other embodiments, the drug delivery device 400 is generally configured and used similar to that discussed above except that the drug holder 402 is not inserted into the distal foot 408*f* in the proximal direction of arrow 414. Instead, the drug holder 402 is preloaded into the dispensing head 404 and is inserted into the proximal head 408*h* in a distal direction during the coupling of the dispensing head 404 (and integral depth guide 406) to the one or more reusable components 408.

In yet other embodiments, the drug delivery device 400 is generally configured and used similar to that discussed above except that the drug holder 402 is not inserted into the distal foot 408*f* in the proximal direction of arrow 414. Instead, the drug holder 402 is inserted into the proximal head 408*h* in a distal direction before the coupling of the dispensing head 404 (and integral depth guide 406) to the one or more reusable components 408.

Figure 7:
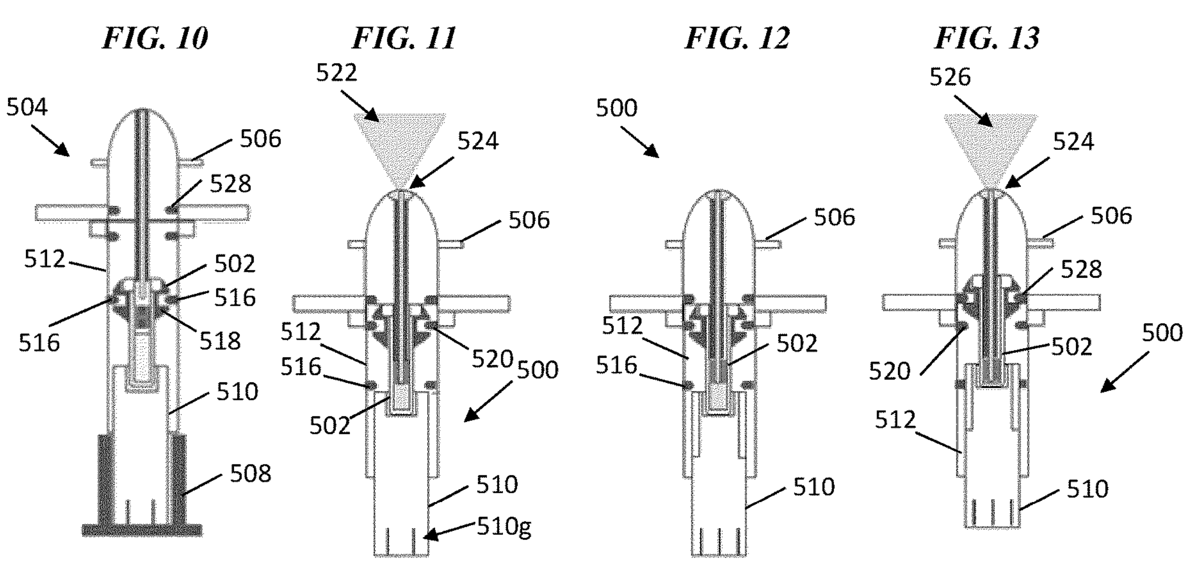
FIG. 7 is an exploded side cross-sectional view of the drug delivery device of FIG. 6 including disposable components and reusable components.

FIG. 6 illustrates another exemplary embodiment of the drug delivery device 200 of FIG. 2 that includes one or more reusable components and one or more disposable components. This illustrated embodiment of a drug delivery device 500 is generally configured and used similar to the drug delivery device 400 of FIG. 4. However, the drug delivery device 500 of FIG. 6 includes a drug holder 502 configured to be inserted into a proximal head 510*h* of the drug delivery device's one or more reusable components in a distal direction before the coupling of the drug delivery device's dispensing head 504 (and integral depth guide 506) to the one or more reusable components. In this illustrated embodiment of a drug delivery device 500, as shown in FIG. 7, the one or more disposable components of the drug delivery device 400 include the drug holder 502, the dispensing head 504, and the depth guide 506, and the one or more reusable components of the drug delivery device 500 include a remainder of the drug delivery device 500.

A loading accessory 508 configured to facilitate coupling of the drug holder 502 to the drug delivery device 500 is also included in the one or more reusable components. In this illustrated embodiment, the one or more reusable components of the drug delivery device 400 are fixedly attached to one another except for the loading accessory 508, which is configured to be releasably coupled to the other of the one or more reusable components.

The drug delivery device 500 in the illustrated embodiment of FIG. 6 is not powered, e.g., does not include any electrical components such as a processor, a sensor, a memory, a communications interface, etc.

FIG. 6 illustrates the drug delivery device 500 with the one or more reusable components thereof coupled to the one or more disposable components thereof. In an exemplary method of coupling the one or more reusable components thereof coupled to the one or more disposable components, as shown in FIG. 8, an actuator 510 of the drug delivery device 500 is coupled to the loading accessory 508 such that at least a distal portion of the actuator 510 is seated in a proximal-facing cavity 512 of the loading accessory 508. The actuator 510 in this illustrated embodiment includes a plunger. As shown in FIG. 9, the drug holder 502 is then inserted into the proximal head 510*h*, which is a proximal portion of the actuator 510, in a distal direction such that a distal portion of the drug holder 502 is seated in a proximal cavity 510*c* formed in the actuator 510.

The dispensing head 504 (and integral depth guide 506) and a body 512 of the drug delivery device 500 are then coupled to the drug holder 502, as shown in FIG. 10, so as to be coupled to the drug holder 502 and the actuator 510. The dispensing head 504 and the body 512 are advanced in a distal direction relative to the drug holder 502 and the actuator 510 until a distal surface of the body 512 abuts a proximal surface of the loading accessory 508, as shown in FIG. 10. The body 512 being coupled to the drug holder 502 allows a coupling mechanism 514 of the drug holder 504 to couple to a coupling feature 516 of the body 512. The coupling mechanism 514 in this illustrated embodiment includes a rib of a proximal sheath 518 that is fixedly coupled to a proximal portion of the drug holder 502. The proximal sheath 518 allows for existing drug holders to be used in the drug delivery device 500, as the proximal sheath 518 can be retrofit to existing drug holders. In other embodiments, the drug holder 502 is manufactured with the proximal sheath 518 as an integral part thereof. The rib extends circumferentially around the sheath 518, which may facilitate engagement of the drug holder 502 with the body 512 regardless of a rotational orientation at which the drug holder 502 is positioned relative to the body 512. In other embodiments, the rib can include one or more arcuate extensions so as to form an arc (one extension) or a broken ring (a plurality of extensions) around the circumference of the drug holder 502. The coupling feature 516 in this illustrated embodiment includes a protrusion configured to be seated in the rib. The protrusion extends circumferentially around the body 512 in this illustrated embodiment, although the protrusion can have another configuration similar to that discussed above regarding the drug holder's rib. The distal advancement of the body 512 relative to and over the drug holder automatically causes the coupling of the coupling mechanism 514 and the coupling feature 516 by the protrusion being automatically seated in the rib. The abutment of the distal surface of the body 512 abutting the proximal surface of the loading accessory 508 ensures that the body 512 has been advanced a sufficient distal distance for the coupling of the coupling mechanism 514 and the coupling feature 516 to occur. The body 512 and the dispensing head 504 can be coupled to the drug holder 502 and the actuator 510 as a unit, or the body 512 can be coupled to the drug holder 502 and the actuator 510 and then the dispensing head 504 can be coupled to the body 512, the drug holder 502, and the actuator 510.

With the body 512 and the dispensing head 504 having been coupled to the drug holder 502 and the actuator 510, the drug delivery device 500 is removed from the loading accessory 508 and is in an initial configuration ready for drug delivery. FIG. 6 shows the drug delivery device 500 after removal from the loading accessory 508.

With the drug delivery device 500 in the initial configuration, the actuator 510 is pushed proximally relative to the body 512 and the dispensing head 504 to cause a first drug spray 522 out of the drug delivery device's opening 524, as shown in FIG. 11. As in this illustrated embodiment, the actuator 510 can include a gripping feature 510*g* to facilitate user grip of the actuator 510. The gripping feature 510*g* includes a plurality of longitudinal grooves formed in the actuator 510 in this illustrated embodiment but can have other configurations, e.g., a textured surface, finger depressions formed in the actuator 510, a rubber cover, etc. The proximal movement of the actuator 510 causes corresponding proximal movement of the drug holder 502 relative to the body 512 and the dispensing head 504 due to the drug holder 502 being seated in the cavity 510*c* of the actuator 510. The proximal movement of the drug holder 502 causes the coupling mechanism 514 and the coupling feature 516 to become decoupled, e.g., for the protrusion to "pop" out of the rib. The actuator 510 is pushed proximally until the actuator 510 abuts the coupling feature 514, e.g., the proximal surface of the actuator 510 abuts a distal surface of the protrusion, and the coupling mechanism 514 of the drug holder 502 couples to a second coupling feature 520 of the body 512 that is proximal to the coupling feature 516. The second coupling feature 520 includes a protrusion similar to the distal coupling feature 516. The distal coupling feature 516 of the body 512 acts as a stop to halt proximal movement of the actuator 510, with the user being able to feel resistance provided to the actuator 510 by the coupling feature 516.

After the first drug spray 522 has been delivered, as shown in FIG. 12, the actuator 510 is pushed proximally again to relative to the body 512 and the dispensing head 504 to cause a second drug spray 526 out of the drug delivery device's opening 524, as shown in FIG. 13. The proximal movement of the actuator 510 causes corresponding proximal movement of the drug holder 502 relative to the body 512 and the dispensing head 504 due to the drug holder 502 still being seated in the cavity 510*c* of the actuator 510. The proximal movement of the drug holder 502 causes the coupling mechanism 514 and the second coupling feature 520 to become decoupled, e.g., for the second protrusion to "pop" out of the rib. The actuator 510 is pushed proximally until the coupling mechanism 514 of the drug holder 502 couples to a coupling feature 528 of the dispensing head 504 that is proximal to the coupling features 516, 520 of the body 512. The dispensing head's coupling feature 528 includes a protrusion similar to the distal coupling feature 516.

After the second drug spray 526 has been delivered, the reusable components of the drug delivery device 500, e.g., the body 512 and the actuator 510, are decoupled from the disposable components of the drug delivery device 500, e.g., the drug holder 502 (including the sheath 518) and the dispensing head 504. The loading accessory 508 is also a reusable component, as mentioned above and as shown in FIG. 13. The coupling of the drug holder's coupling mechanism 514 and the dispensing head's coupling feature 528 allows the drug holder 502 to be removed with the dispensing head 504 from the reusable components.

In the embodiment of FIGS. 6-13, a piercing element 530 configured to pierce or puncture a seal member 532 of the drug holder 502 extends distally from the dispensing head 504. Before the dispensing head 504 is coupled to the drug holder 502, the piercing element 530 is exposed. In some embodiments, as shown in FIGS. 14-16, the drug delivery device 500 can include a shield 534 configured to provide a shield around the piercing element 530 prior to the dispensing head's coupling to the drug holder 502, which may help prevent the piercing element 530 from piercing or puncturing a user or other unintended object. FIG. 14 illustrates the drug delivery device 500 after two drug sprays have occurred. FIG. 15 illustrates the drug delivery device 500 after the body 512 and the actuator 510 have been decoupled from the drug holder 502 (including the sheath 518), the dispensing head 504, and the shield 534 that is fixedly coupled to the dispensing head 504. In this illustrated embodiment, as shown in FIG. 16, the reusable components of the drug delivery device 500 include the body 512, the actuator 510, and the dispensing head 504 (including the shield 534), and the disposable components of the drug delivery device 500 include the drug holder 502. The loading accessory 508 is also a reusable component, as mentioned above and as shown in FIG. 16.

Figure 17:
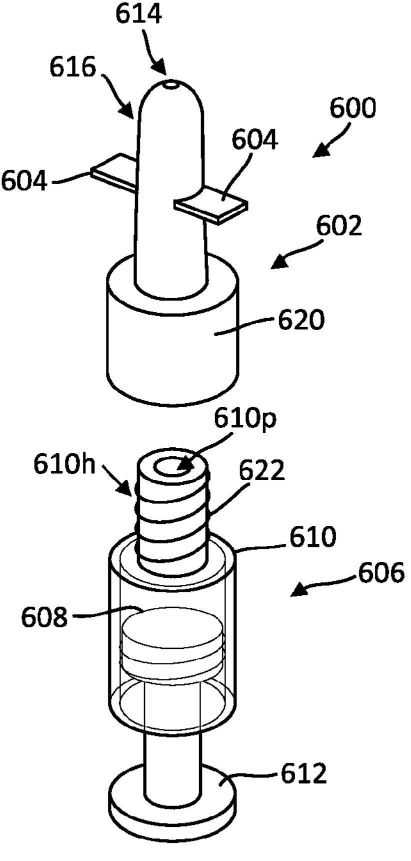
FIG. 17 is an exploded view of another embodiment of the drug delivery device of FIG. 2.

FIG. 17 illustrates another exemplary embodiment of the drug delivery device 200 of FIG. 2 that includes one or more reusable components and one or more disposable components.

In this illustrated embodiment of a drug delivery device 600, the one or more reusable components of the drug delivery device 600 include a dispensing head 602 and a depth guide 604, and the one or more disposable components 606 of the drug delivery device 600 include a remainder of the drug delivery device 600. The dispensing head 602 and the depth guide 604 are integrated together as one element in this illustrated embodiment. In this illustrated embodiment, the one or more disposable components 606 of the drug delivery device 600 are fixedly attached to one another. FIG. 17 illustrates the one or more reusable components not coupled to the one or more disposable components 606 of the drug delivery device 600.

The drug delivery device 600 in the illustrated embodiment of FIG. 17 is not powered, e.g., does not include any electrical components such as a processor, a sensor, a memory, a communications interface, etc.

In this illustrated embodiment, the drug delivery device 600 is in the form of a syringe that includes a drug holder 608 in the form of a reservoir disposed within a body 610 of the drug delivery device 600 and that includes an actuator 612 in the form of a plunger. The plunger 612 is configured to move relative to the body 610 of the drug delivery device 600 to cause the drug in the drug holder 608 to exit the drug delivery device 600 through an opening 614 in a tip 616 of the dispensing head 602. The actuator 612 is operatively engaged with the drug contained in the drug holder 608. The actuator 612 is configured to move between an initial configuration, which is shown in FIG. 17, to an actuated configuration, by being pushed in a proximal direction, e.g., by being manually pushed by a user, toward the drug holder 608 and the dispensing head 602.

The dispensing head 602 includes a coupling feature configured to be to a coupling mechanism of the one or more disposable components 606 of the drug delivery device 600. The coupling mechanism and the coupling feature can have a variety of configurations, as discussed above with respect to the drug delivery device 400 of FIG. 4. In this illustrated embodiment, the coupling feature includes a thread 620 on an internal surface of the dispensing head 602, and the coupling mechanism includes a thread 622 on an external surface of the one or more disposable components 606, e.g., on a proximal head 610*h* of the body 610. To couple the dispensing head 602 (and the depth guide 604) to the one or more disposable components 606, the thread 620 on the dispensing head 602 can be releasably thread with the thread 622 on the one or more reusable components 606. To decouple the dispensing head 602 (and the depth guide 604) from the one or more disposable components 606, the thread 620 on the dispensing head 602 can be unthreaded from the thread 622 on the one or more disposable components 606. The one or more reusable components can then be coupled to another set of one or more disposable components, and so on.

The one or more disposable components 606 includes a seal member configured to provide a fluid tight seal such that the drug is contained in the drug holder 608 until the seal provided by the seal member is broken. The drug contained in the drug holder 606 can thus be prevented from prematurely exiting the drug holder 602 prior to intended drug delivery. The seal member can be positioned at a variety of locations in the one or more disposable components 606. For example, the seal member can be positioned at a proximal opening 610*p* in the proximal head 610*h* of the body. For another example, the seal member can be positioned at a proximal end of the drug holder 608 disposed in the body 610.

The seal provided by the seal member can be broken in a variety of ways, such as by being pierced by a needle of the one or more reusable components, e.g., a needle contained in the dispensing head 602 and in fluid communication with the opening 614, to which the one or more reusable components 606 are releasably coupled. The coupling of the dispensing head 602 can be configured to automatically cause the seal member to be broken, e.g., by the needle being advanced distally far enough into the one or more disposable components 606 to break the seal member. The seal member can have a variety of configurations, as will be appreciated by a person skilled in the art, such as by being a pierceable polymer septum or a foil layer. The seal member can be protected from accidental puncturing or piercing before intended use with a removable protective member or stopper, such as a TE seal, etc. In some embodiments, the seal member can be omitted and instead a removable protective member or stopper can be provided that is removed just prior to coupling of the one or more reusable components and the one or more disposable components.

After the drug has been delivered by the drug delivery device 600, the one or more reusable components can be released from the one or more disposable components 606. In this illustrated embodiment, as discussed above, the decoupling includes unthreading the threads 620, 622.

Figure 18:
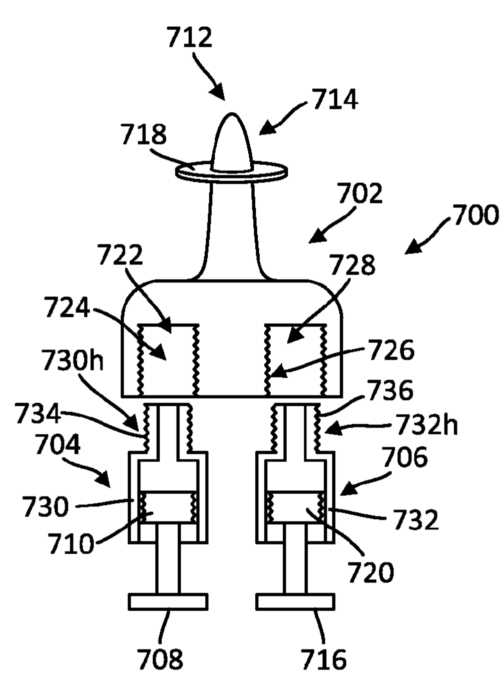
FIG. 18 is an exploded view of yet another embodiment of the drug delivery device of FIG. 2.

FIG. 18 illustrates another exemplary embodiment of the drug delivery device 200 of FIG. 2 that includes one or more reusable components and one or more disposable components. This illustrated embodiment of a drug delivery device 700 is generally configured and used similar to the drug delivery device 600 of FIG. 17. However, the drug delivery device 700 of FIG. 18 includes a dispensing head 702 (and a depth guide 718 integrated therewith) configured to be coupled to two sets of disposable components 704, 706 at a time instead of to only one at a time. The drug delivery device 700 is thus configured to operate in two stages of operation with drug being delivered from the drug delivery device into each of a patient's two nostrils. A first stage of operation includes actuation of a first actuator 708 to deliver a first drug from a first drug holder 710 in a first body 730 through an opening 712 in a tip 714 of the dispensing head 702. A second stage of operation includes actuation of a second actuator 716 to deliver a second drug from a second drug holder 720 in a second body 732 through the opening 712 in the tip 714 of the dispensing head 702. Between the first and second stages of operation, the tip 714 can be repositioned from one of the patient's nostrils to the other of the patient's nostrils.

The coupling mechanism in this illustrated embodiment includes a first thread 722 on an internal surface of a first cavity 724 of the dispensing head 702 and a second thread 726 on an internal surface of a second cavity 728 of the dispensing head 702. The first thread 722 is configured to couple to a first coupling feature of the first set of disposable components 704, which includes a thread 734 on an external surface of the first set of disposable components 704, e.g., on a proximal head 730*h* of the first body 730. The second thread 726 is configured to couple to a first coupling feature of the second set of disposable components 706, which includes a thread 736 on an external surface of the second set of disposable components 706, e.g., on a proximal head 732*h* of the second body 732. The various threads 722, 726, 734, 736 are configured to be threaded and unthreaded similar to that discussed above regarding the drug delivery device 600 of FIG. 17. The first set of reusable components 704 or the second set of disposable components 706 can be coupled first to the one or more reusable components. The first set of disposable components 704 or the second set of disposable components 706 can be decoupled first from the one or more reusable components. FIG. 18 illustrates the one or more reusable components not coupled to the one or more disposable components 704, 706 of the drug delivery device 700. After decoupling, the one or more reusable components can then be coupled to an additional one or more sets of one or more disposable components, and so on.

In an exemplary embodiment, the drugs in each of the drug holders 710, 720 are the same such that the drug delivery device 700 is usable to deliver subsequent doses of the same drug to a user of the drug delivery device 700. The user may therefore be able to use the same drug delivery device 700 in fulfilling a drug prescription. In other embodiments, the drugs in each of the drug holders 710, 720 are not the same such that the drug delivery device 700 is usable to deliver doses of different drugs to a user of the drug delivery device 700. The user may therefore be able to use the same drug delivery device 700 repeatedly in fulfilling different drug prescriptions. In embodiments in which the drugs in each of the drug holders 710, 720 are the same, one of the drug holders 710, 720 contains a first drug therein and the other one of the drug holders 710, 720 contains a second drug that is different than the first drug. In embodiments in which an additional one or more sets of one or more disposable components are provided for releasable coupling to the one or more reusable components, the number of different drugs contained in the various drug holders can be more than two.

In at least some embodiments, the one or more reusable components of a drug delivery device can be reconditioned for reuse after at least one use. Reconditioning can include any combination of the steps of disassembly of the one or more reusable components of the drug delivery device, followed by cleaning or replacement of particular pieces and subsequent reassembly. In particular, the one or more reusable components of the drug delivery device can be disassembled, and any number of the particular pieces or parts of the one or more reusable components of the drug delivery device can be selectively replaced or removed in any combination. Upon cleaning and/or replacement of particular parts, the one or more reusable components of the drug delivery device can be reassembled for subsequent use either at a reconditioning facility, or by a health care provider immediately prior to use. A person skilled in the art will appreciate that reconditioning of the one or more reusable components of a drug delivery device can utilize a variety of techniques for disassembly, cleaning/replacement, and reassembly. Use of such techniques, and the resulting reconditioned one or more reusable components of drug delivery device, are all within the scope of the present application.

The present disclosure has been described above by way of example only within the context of the overall disclosure provided herein. It will be appreciated that modifications within the spirit and scope of the claims may be made without departing from the overall scope of the present disclosure.

What is claimed is:

1. A drug delivery system, comprising:

a dispensing head including a tip configured to be positioned in a nose of a patient, the tip having an opening therein;

a drug holder containing a drug therein; and a body including a distal coupler configured to releasably couple to a coupler of the drug holder, and the body including a proximal coupler configured to releasably couple to a coupler of the dispensing head;

wherein the drug delivery system is configured such the drug holder is not coupled to the coupler of the dispensing head while the drug is initially delivered out of the opening, and, after initiation of delivery of the drug out of the opening, the drug holder and the coupler of the dispensing head are coupled to one another such that the drug holder and dispending head are configured to be released from the proximal coupler as a unit.

2. The system of claim 1, wherein the drug holder is configured to be at least partially disposed within the dispensing head after the drug has been delivered out of the opening to allow the drug holder and the dispensing head to be released from the proximal coupler as the unit after the drug has been delivered out of the opening.

3. The system of claim 1, wherein the proximal coupler includes a thread, and the coupler of the dispensing head includes a thread configured to mate with the thread of the proximal coupler.

4. The system of claim 1, wherein the coupler of the dispensing head includes a clip configured to clip to the proximal coupler.

5. The system of claim 1, wherein one of the proximal coupler and the coupler of the dispensing head includes one or more protrusions, and the other of the proximal coupler and the coupler of the dispensing head includes one or more grooves or depressions configured to seat the one or more protrusions therein.

6. The system of claim 1, wherein the coupler of the dispensing head is on a distal base of the dispensing head that is configured to be manually pressed by a user to cause the drug to be delivered out of the opening.

7. The system of claim 1, further comprising a depth guide attached to the dispensing head configured to facilitate guiding the tip into the nose at a depth.

8. The system of claim 1, wherein the drug is one of ketamine, esketamine, naloxone, and sumatriptan.

9. The system of claim 1, further comprising:

a second dispensing head including a second tip configured to be positioned in the nose of the patient, the second tip having a second opening therein; and a second drug holder containing a second drug therein; wherein;

the second drug holder comprises a second coupler configured to releasably couple to the distal coupler after the drug holder and the dispensing head have been released from the proximal coupler, a second coupler of the second dispensing head is configured to releasably couple to the proximal coupler after the drug holder and the dispensing head have been released from the proximal coupler, the drug delivery system is configured such that the second drug holder is not coupled to the second coupler of the second dispensing head while the second drug is initially delivered out of the second opening, and, after initiation of delivery of the second drug out of the second opening, the second drug holder and the second coupler of the second dispensing head are coupled to one another such that the second drug holder and second dispensing head are configured to be released from the proximal coupler as a unit.

10. The system of claim 9, wherein the drug is one of ketamine, esketamine, naloxone, and sumatriptan; and the second drug is one of ketamine, esketamine, naloxone, and sumatriptan.

11. The system of claim 10, wherein the drug and the second drug are the same.

12. The system of claim 10, wherein the drug and the second drug are different.

13. A drug delivery method, comprising:

coupling a first dispensing head to a first coupler of a body, wherein the first dispensing head includes a coupler;

coupling a first drug holder to a second coupler of the body such that the first drug holder is not coupled to the coupler of the first dispensing head, the first drug holder containing a first drug therein;

after coupling the first dispensing head and the first drug holder to the body, causing the first drug to exit the first drug holder and spray out an opening of a tip of the first dispensing head that is positioned in a nose of a patient and causing the first drug holder and the coupler of the first dispensing head to become coupled to one another;

removing the first dispensing head and the first drug holder as a unit from the body and subsequently coupling a second dispensing head to the first coupler of the body, the second dispensing head including a coupler and coupling a second drug holder to the second coupler of the body such that the second drug holder is not coupled to the coupler of the second dispensing head, the second drug holder containing a second drug therein; and after coupling the second dispensing head and the second drug holder to the body, causing the second drug to exit the second drug holder and spray out a second opening of a second tip of the second dispensing head that is positioned in the nose of the patient and causing the second drug holder and the coupler of the second dispensing head to become coupled to one another.

14. The method of claim 13, wherein the drug holder is at least partially disposed within the dispensing head after the first drug has exited the drug holder to allow the drug holder and the first dispensing head to be removed as the unit.

15. The method of claim 13, wherein the first coupler includes a thread, and coupling the first dispensing head to the body includes mating the first dispensing head to the thread of the first coupler.

16. The method of claim 13, wherein coupling the first dispensing head to the body includes clipping the first dispensing head to the first coupling-featurecoupler.

17. The method of claim 13, wherein the first coupler includes one or more protrusions, and coupling the first dispensing head to the body includes seating the one or more protrusions in one or more grooves or depressions of the dispensing head.

18. The method of claim 13, wherein the first coupler includes one or more grooves or depressions, and coupling the first dispensing head to the body includes seating one or more protrusions of the dispensing head in the one or more grooves or depressions.

19. The method of claim 13, wherein causing the first drug to exit the first drug holder includes pushing the first dispensing head relative to the body; and causing the second drug to exit the second drug holder includes pushing the second dispensing head relative to the body.

20. The method of claim 13, wherein the first drug is one of ketamine, esketamine, naloxone, and sumatriptan; and the second drug is one of ketamine, esketamine, naloxone, and sumatriptan.

21. The method of claim 20, wherein the first drug and the second drug are the same.

22. The method of claim 20, wherein the first drug and the second drug are different.

* * * * *